United States Patent
Wang et al.

(10) Patent No.: US 6,673,821 B2
(45) Date of Patent: Jan. 6, 2004

(54) NITROGEN HETEROCYCLE INHIBITORS OF ASPARTYL PROTEASE

(75) Inventors: Guoqiang Wang, Cambridge, MA (US); Yat Sun Or, Cambridge, MA (US); John Rougas, Brighton, MA (US); Steven Wayne Riesinger, Stoneham, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 22 days.

(21) Appl. No.: 10/007,342

(22) Filed: Oct. 22, 2001

(65) Prior Publication Data

US 2003/0114500 A1 Jun. 19, 2003

(51) Int. Cl.7 .................. A61K 31/426; A61K 31/427; A61K 31/4439; A61K 31/4709; C07D 277/04
(52) U.S. Cl. .................. 514/365; 548/146; 546/135; 546/269.7; 514/342
(58) Field of Search .................. 548/146; 514/365, 514/342; 546/135, 269.7

(56) References Cited

PUBLICATIONS

Mimoto et al.; *Journal of Medicinal Chemistry*, 1999, vol. 42, No. 10, pp. 1789–1802.
T. Kimura et al.; *Bioorganic & Medicinal Chemistry Letters*, 9 (1999), pp. 803–806.

*Primary Examiner*—Deborah C. Lambkin
*Assistant Examiner*—Rebecca Anderson
(74) *Attorney, Agent, or Firm*—Jason D. Ferrone

(57) ABSTRACT

Nitrogen heterocycles that inhibit aspartyl protease are disclosed, as are methods of treating diseases, particularly HIV, using these compounds. The compounds have the formula:

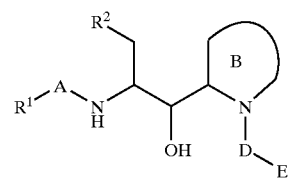

A representative example is:

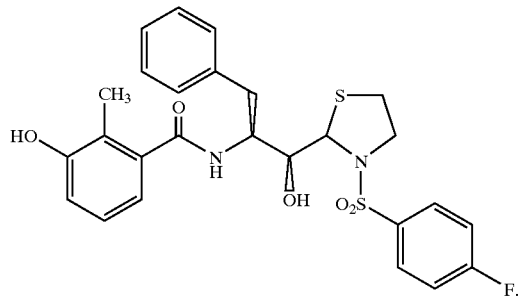

4 Claims, No Drawings

NITROGEN HETEROCYCLE INHIBITORS OF ASPARTYL PROTEASE

FIELD OF THE INVENTION

The present invention relates to nitrogen heterocycles that inhibit aspartyl protease and to methods of treating diseases using these compounds.

BACKGROUND OF THE INVENTION

The human immunodeficiency virus ("HIV") is the causative agent for acquired immunodeficiency syndrome ("AIDS")—a disease characterized by the destruction of the immune system, particularly of CD4+ T-cells, with attendant susceptibility to opportunistic infections—and its precursor AIDS-related complex ("ARC")—a syndrome characterized by symptoms such as persistent generalized lymphadenopathy, fever and weight loss. As in the case of several other retroviruses, HIV encodes the production of a protease which carries out post-translational cleavage of precursor polypeptides in a process necessary for the formation of infectious virions. A number of synthetic anti-viral agents have been designed to target various stages in the replication cycle of HIV. These agents include compounds which block viral binding to CD4+ T-lymphocytes (for example, soluble CD4), and compounds which interfere with viral replication by inhibiting viral reverse transcriptase (for example, didanosine and zidovudine (AZT)) and inhibit integration of viral DNA into cellular DNA. However, such agents, which are directed primarily to early stages of viral replication, do not prevent the production of infectious virions in chronically infected cells. Furthermore, administration of some of these agents in effective amounts has led to cell-toxicity and unwanted side effects, such as anemia and bone marrow suppression.

More recently, the focus of anti-viral drug design has been to create compounds which inhibit the formation of infectious virions by interfering with the processing of viral polyprotein precursors. Processing of these precursor proteins requires the action of virus-encoded proteases which are essential for replication. The anti-viral potential of HIV protease inhibition has been demonstrated using peptidal inhibitors. Such peptidal compounds, however, are typically large and complex molecules that tend to exhibit poor bioavailability and are not generally efficacious on oral administration. Accordingly, the need still exists for compounds that can effectively inhibit the action of viral proteases, particularly aspartyl proteases, for use as agents for preventing and treating chronic and acute viral infections.

In addition, aspartyl protease inhibitors are of interest for developing antimalarial drugs. Resistance to known antimalarial therapies is becoming an increasing problem, and new therapies are therefore desperately needed. Upon infecting a host, the malaria parasite avidly consumes the host hemoglobin as its source of nutrients. Plasmepsin I and II are proteases from *Plasmodium falciparum* that are necessary during the initial stages of hemoglobin hydrolysis and digestion. It has been shown that inhibition of plasmepsin by a peptidomimetic inhibitor is effective in preventing malarial hemoglobin degradation and in killing the parasite. Thus, persons skilled in the art expect that plasmepsin inhibitors will provide effective antimalarial therapy.

Another aspartyl protease, cathepsin D, has been implicated in a variety of diseases, including connective tissue disease, muscular dystrophy, and breast cancer. The enzyme is also believed to be the protease which processes the beta-amyloid precursor protein (Dreyer, R. N. et al. Eur. J. Biochem (1994), 244, 265–271 and Ladror, U. S. et al. J. Biol. Chem. (1994), 269, 12422–18428) generating the major component of plaques in the brains of Alzheimer's patients. Consequently, persons of skill in the art expect that inhibitors of cathepsin D will be useful in treating Alzheimer's disease.

Other human aspartyl proteases, such as renin, are involved in the maintenance of blood pressure, and inhibitors of these proteases find use as treatments for hypertension. Inhibitors of aspartyl proteases that process endothelin precursors are similarly useful blocking vasoconstriction.

SUMMARY OF THE INVENTION

It has now been discovered that certain nitrogen heterocycles and pharmaceutically acceptable salts thereof, are useful as inhibitors of aspartyl proteases, in particular, HIV aspartyl protease. These compounds can be used alone or in combination with other therapeutic or prophylactic agents, such as anti-virals, antibiotics, immunomodulators or vaccines, for the treatment or prophylaxis of viral infection. The compounds of this invention are capable of inhibiting HIV viral replication in human CD4+ T-cells and are useful as therapeutic and prophylactic agents to treat or prevent infection by HIV-1 and related viruses which may result in asymptomatic infection, AIDS-related complex ("ARC"), acquired immunodeficiency syndrome ("AIDS"), or similar disease of the immune system.

Therefore, in one aspect, the present invention relates to compounds of formula

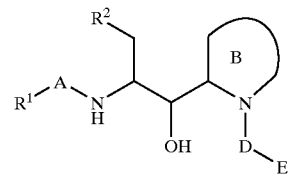

wherein $R^1$ is chosen from the group consisting of $C_1$–$C_{20}$ alkyl, aryl, alkylaryl, substituted alkylaryl, $C_1$–$C_{10}$ alkoxy, $C_3$–$C_{10}$ oxaalkyl, aryloxy, substituted aryl, substituted aryloxy, heterocyclyl and heterocyclyloxy;

$R^2$ is chosen from the group consisting of $C_1$–$C_{10}$ hydrocarbon, substituted aryl and heterocyclyl;

A is chosen from the group consisting of a direct bond, —$SO_2$—, $NHSO_2$—,

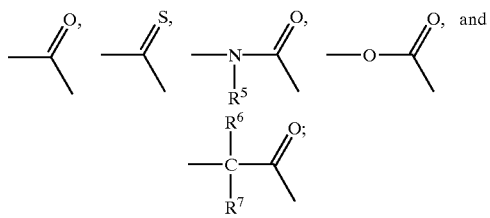

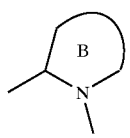

is a monocyclic, bicyclic or tricyclic nitrogen heterocycle containing from 0 to 3 substituents chosen from lower alkyl, lower alkoxy, lower alkylthio, hydroxy, mercapto, cyano, carboxy, lower alkoxycarbonyl, lower alkylaminocarbonyl, amino, lower alkylamino, di(lower alkyl)amino, nitro, halo and haloalkyl;

$R^5$, $R^6$ and $R^7$ are chosen independently from the group consisting of hydrogen and lower alkyl;

D is chosen from the group consisting of —$SO_2$—,

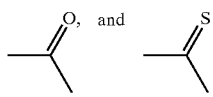

E is chosen from the group consisting of $C_1$–$C_{10}$ hydrocarbon, substituted aryl, heterocyclyl and substituted heterocyclyl.

In another aspect, the invention relates to a method of treating or preventing a protease-precipitated disease which comprises administering a therapeutically effective amount of a compound of the formula shown above.

In another aspect, the invention relates to a pharmaceutical composition comprising a pharmaceutically acceptable carrier and a compound of the formula shown above, or a pharmaceutically acceptable salt thereof.

DETAILED DESCRIPTION OF THE INVENTION

The present invention relates to compounds of formula

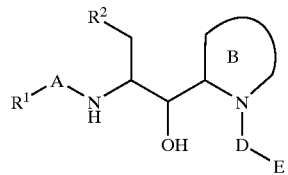

as described above. Preferred subgenera are those in which:

(1) A is

and $R^1$ is $C_1$–$C_{20}$ alkyl, aryl, alkylaryl, or substituted aryl; or (2) A is

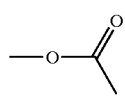

and $R^1$ is $C_1$–$C_{20}$ alkyl, $C_1$–$C_{10}$ oxaalkyl, substituted aryl or heterocyclyl; or (3) A is

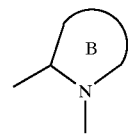

and $R^1$ is substituted aryl or substituted aryloxy

Other preferred subgenera are those in which

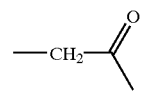

is a monocyclic nitrogen heterocycle, preferably pyrrolidine, thiazolidine, oxazolidine, piperidine, morpholine, hexahydroazepine, imidazolidine, imidazoline, dihydrothiazole, dihydrooxazole, imidazole, indoline, indole, benzimidazole, tetrahydroquinoline or tetrahydroisoquinoline; most preferably pyrrolidine, thiazolidine or oxazolidine. Other preferred subgenera are those in which D is —$SO_2$— and E is chosen from aryl, heteroaryl, substituted aryl and substituted heteroaryl.

One representative subgenus is that of formula:

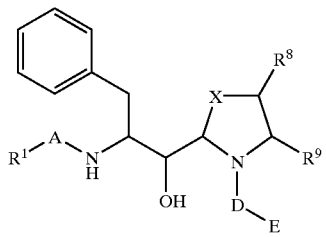

In this genus X is —O—, —S—, —NH— or —$CH_2$—; and $R^8$ and $R^9$ can each be hydrogen, lower alkyl, lower alkoxy, lower alkylthio, phenyl, hydroxy, mercapto, cyano, carboxy, lower alkoxycarbonyl, lower alkylaminocarbonyl, amino, lower alkylamino, di(lower alkyl)amino, nitro, halo or haloalkyl. Compounds in which X is —O—, —S— and —$CH_2$— and $R^8$ and $R^9$ are hydrogen, lower alkyl, lower alkoxy or phenyl are preferred. When X is S and D is —$SO_2$— or —C(O)—, E is preferably aryl, heteroaryl, substituted aryl or substituted heteroaryl. In these compounds, when D is —$SO_2$—, E is preferably substituted phenyl. In this subgenus, preferred compounds are those in which (1) A is a direct bond and $R^1$ is lower alkyl; or (2) A is —C(O)— and $R^1$ is substituted phenyl, lower alkoxy, $C_3$–$C_6$ oxaalkyl, or heterocyclyloxy; or (3) A is —$CH_2$C(O)— and $R^1$ is substituted phenoxy.

Another preferred subgenus is of formula

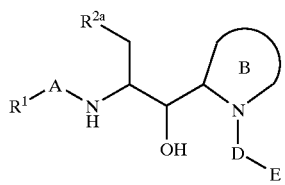

wherein $R^{2a}$ is phenyl, ethyl, propyl or butyl. In this subgenus, the carbon marked S* is preferably of the S configuration and the carbon marked R* is preferably of the R configuration:

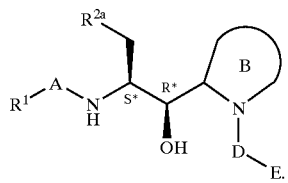

Diseases that may be treated or prevented using the compounds of the invention include retroviral infections, malaria, hypertension, connective tissue disease, muscular dystrophy, breast cancer and Alzheimer's disease. These are collectively referred to herein as protease-precipitated diseases.

Definitions

Throughout this specification the terms and substituents retain their definitions.

The term "preventing" as used herein refers to administering a medicament beforehand to forestall or obtund an attack. The person of ordinary skill in the medical art (to which the present method claims are directed) recognizes that the term "prevent" is not an absolute term. In the medical art it is understood to refer to the prophylactic administration of a drug to substantially diminish the likelihood or seriousness of a condition, and this is the sense intended in applicants' claims. As used herein, reference to "treatment" of a patient is intended to include prophylaxis.

Alkyl is intended to include linear, branched, or cyclic hydrocarbon structures and combinations thereof. Lower alkyl refers to alkyl groups of from 1 to 6 carbon atoms. Examples of lower alkyl groups include methyl, ethyl, propyl (i.e., n-propyl and isopropyl), butyl (i.e., n-butyl, i-butyl, s-butyl and t-butyl) and the like. Preferred alkyl groups are those of $C_{20}$ or below. Cycloalkyl is a subset of alkyl and includes cyclic hydrocarbon groups of from 3 to 8 carbon atoms. Examples of cycloalkyl groups include c-propyl, c-butyl, c-pentyl, norbornyl and the like.

$C_1$ to $C_{10}$ Hydrocarbon includes alkyl, cycloalkyl, alkenyl, alkynyl, aryl and combinations thereof. Examples include phenethyl, cyclohexylmethyl, norbornyl and naphthylethyl.

Alkoxy or alkoxyl refers to groups of from 1 to 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. Lower-alkoxy refers to groups containing one to four carbons.

Oxaalkyl refers to alkyl residues in which one or more carbons has been replaced by oxygen. Examples include methoxypropoxy, 3,6,9-trioxadecyl and the like.

Acyl refers to groups of from 1 to 8 carbon atoms of a straight, branched, cyclic configuration, saturated, unsaturated and aromatic and combinations thereof, attached to the parent structure through an carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. Lower-acyl refers to groups containing one to four carbons.

Aryl and heteroaryl mean a 5- or 6-membered aromatic or heteroaromatic ring containing 0–3 heteroatoms selected from O, N, or S; a bicyclic 9- or 10-membered aromatic or heteroaromatic ring system containing 0–3 heteroatoms selected from O, N, or S; or a tricyclic 13- or 14-membered aromatic or heteroaromatic ring system containing 0–3 heteroatoms selected from O, N, or S. The aromatic 6- to 14-membered carbocyclic rings include, e.g., benzene, naphthalene, indane, tetralin, and fluorene and the 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

Arylalkyl means an alkyl residue attached to an aryl ring. Examples are benzyl, phenethyl and the like.

Heteroarylalkyl means an alkyl residue attached to a heteroaryl ring. Examples include, e.g., pyridinylmethyl, pyrimidinylethyl and the like.

Heterocycle means a cycloalkyl or aryl residue in which from one to three carbons is replaced by a heteroatom selected from the group consisting of N, O and S. The nitrogen and sulfur heteroatoms may optionally be oxidized, and the nitrogen heteroatom may optionally be quaternized. Examples of heterocycles that fall within the scope of the invention include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pytimidine, thiophene, furan, oxazole, oxazoline, isoxazole, dioxane, tetrahydrofuran and the like. It is to be noted that heteroaryl is a subset of heterocycle in which the heterocycle is aromatic. Examples of heterocyclyl residues additionally include piperazinyl, 2-oxopiperazinyl, 2-oxopiperidinyl, 2-oxo-pyrrolidinyl, 2-oxoazepinyl, azepinyl, 4-piperidinyl, pyrazolidinyl, imidazolyl, imidazolinyl, imidazolidinyl, pyrazinyl, oxazolidinyl, isoxazolidinyl, thiazolidinyl, isothiazolyl, quinuclidinyl, isothiazolidinyl, benzimidazolyl, thiadiazolyl, benzopyranyl, benzothiazolyl, tetrahydrofuryl, tetrahydropyranyl, thienyl, benzothienyl, thiamorpholinyl, thiamorpholinylsulfoxide, thiamorpholinylsulfone, oxadiazolyl, triazolyl, thioxanthine, phenothiazine and tetrahydroquinolinyl.

Substituted alkyl, aryl, cycloalkyl, heterocyclyl etc. refer to alkyl, aryl, cycloalkyl, or heterocyclyl wherein up to three H atoms in each residue are replaced with halogen, haloalkyl, hydroxy, loweralkoxy, hydroxy loweralkyl, carboxy, carboalkoxy (also referred to as alkoxycarbonyl), carboxamido (also referred to as alkylaminocarbonyl), cyano, carbonyl, nitro, amino, alkylamino, dialkylamino, mercapto, alkylthio, sulfoxide, sulfone, acylamino, amidino, phenyl, benzyl, heteroaryl, phenoxy, benzyloxy, or heteroaryloxy.

The term "halogen" means fluorine, chlorine, bromine or iodine.

The compounds described herein contain two or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as, their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., Enantiomers, Racemates, and Resolutions, John Wiley & Sons 1981. When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon—carbon double bond appearing herein is selected for convenience only and is not intended to designate a particular configuration unless the text so states; thus a carbon—carbon double bond depicted arbitrarily herein as trans may be cis, trans, or a mixture of the two in any proportion.

The graphic representations of racemic, ambiscalemic and scalemic or enantiomerically pure compounds used herein are taken from Maehr *J. Chem. Ed.* 62, 114–120 (1985): solid and broken wedges are used to denote the absolute configuration of a chiral element; wavy lines indicate disavowal of any stereochemical implication which the bond it represents could generate; solid and broken bold lines are geometric descriptors indicating the relative configuration shown but denoting racemic character; and wedge outlines and dotted or broken lines denote enantiomerically pure compounds of indeterminate absolute configuration.

Terminology related to "protecting", "deprotecting" and "protected" functionalities occurs throughout this application. Such terminology is well understood by persons of skill in the art and is used in the context of processes which involve sequential treatment with a series of reagents. In that context, a protecting group refers to a group which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes of the invention, the person of ordinary skill can readily envision those groups that would be suitable as "protecting groups". In the case of the present invention, the functionalities that must be protected are most commonly carboxylic acids, amines and alcohols. Suitable groups for that purpose are discussed in standard textbooks in the field of chemistry, such as *Protective Groups in Organic Synthesis* by T. W. Greene [John Wiley & Sons, New York, 1991], which is incorporated herein by reference. The compounds employed as starting materials in the synthesis of the compounds of this invention are well known and, to the extent not commercially available are readily synthesized by standard procedures commonly employed by those of ordinary skill in the art.

The pharmaceutically acceptable salts of the invention are typically formed by reacting a compound, such as that of formula 001153 (see Table 1 below), with an equimolar or excess amount of acid or by reacting a compound, e.g. wherein $R^1$ is carboxyphenyl, with an equimolar or excess amount of base. The reactants are generally combined in a mutual solvent such as diethyl ether or toluene, for acid addition salts, or water or alcohols for base addition salts, and the salts normally precipitate out of solution within about one hour to about ten days and can be isolated by filtration or other conventional methods. In addition, some of the compounds of the invention may form solvates with water or with common organic solvents, and such solvates are included within the scope of the compounds of the present invention.

Scheme I details a method for the production of compound 5, which is a useful precursor of compounds of the invention. Table I, which follows the scheme, illustrates the compounds that can be synthesized by Scheme I, but Scheme I is not limited by the compounds in the tables nor by any particular substituents employed in the schemes for illustrative purposes. The examples illustrate the application of the synthesis described in Scheme I to specific compounds.

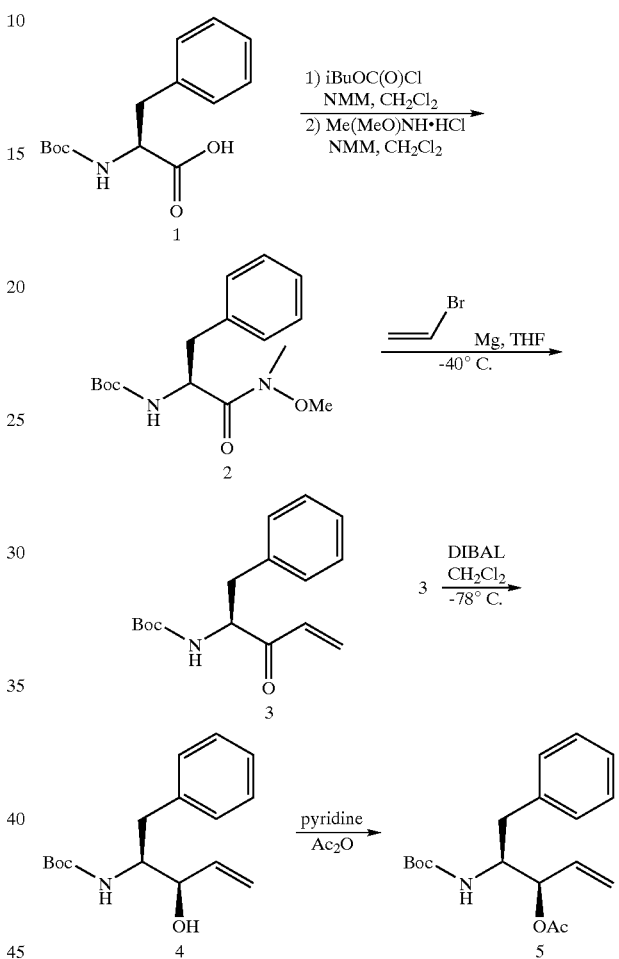

Amide couplings used to form compounds of this invention are typically performed by the use of the carbodiimide method with reagents such as dicyclohexylcarbodiimide or 1-ethyl-3-(3-dimethylaminopropyl) carbodiimide. Other methods of forming the amide or peptide bond include, but are not limited to the synthetic routes via an acid chloride, azide, mixed anhydride or activated ester. Typically, solution phase amide couplings are performed, but solid-phase synthesis by classical Merrifield techniques may be employed instead. The addition and removal of one or more protecting groups is also typical practice.

A method for the preparation of compound 5 is given by Scheme I. The Weinreb amide of Boc protected L-phenylalanine (compound 2) is prepared via the standard mixed anhydride method. Compound 2 is then alkylated with vinylmagnesium bromide to give compound 3 which is selectively reduced with DIBAL to give compound 4. Compound 4 is acylated under standard conditions with acetic anhydride in pyridine to give compound 5.

Scheme II shows how compounds of the invention can be prepared from the precursor 5.

Scheme II

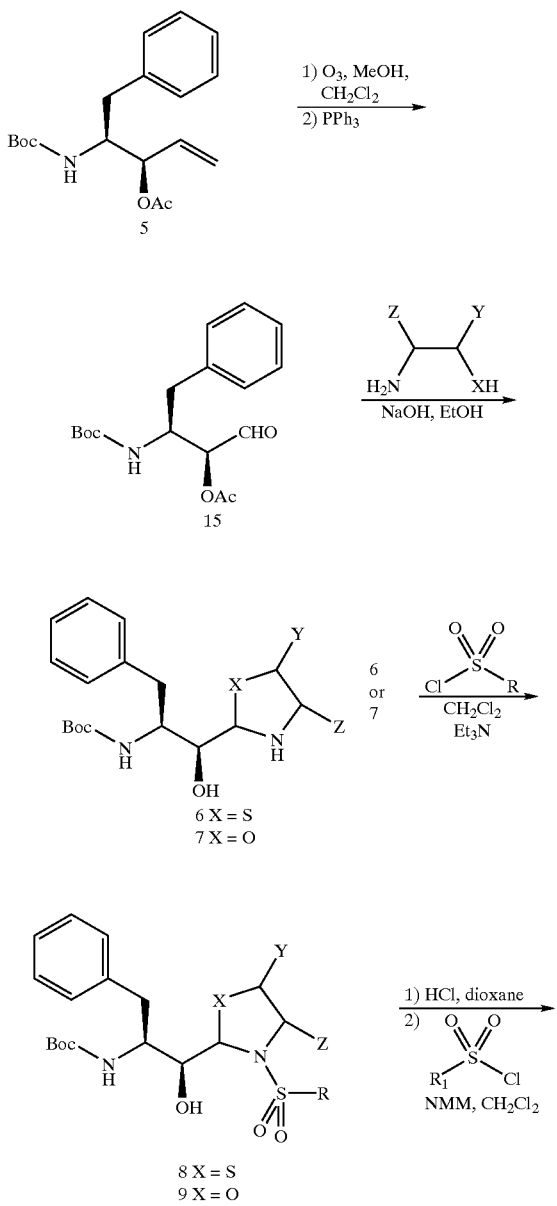

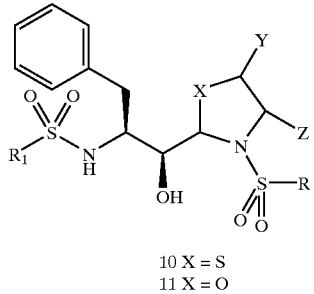

Ozonolysis of 5 and reductive quenching with triphenylphosphine gives the corresponding aldehyde 15. Cyclization of the appropriately substituted amino thioethane or amino alcohol onto the aldehyde under basic conditions gives the thiazolidines 6 or oxazolidine 7 respectively. Reaction of the free amine with the appropriate electrophile gives the corresponding N-substituted derivatives. For illustrative purposes preparation of sulfonamides 8 and 9 via reaction with the sulfonyl chloride is shown, however, one skilled in the art will appreciate that amides, thioamides, ureas, sulfonamides, carbamates, sulfamides and similar structures can also be obtained in analogous reactions using standard conditions. For example, the free amine of compound 8 or 9 can be reacted with isocyanates in a solvent such as $CH_2Cl_2$ in the presence a base such a N-methylmorpholine to generate urea structures, or a sulfonamide group can be formed by the treatment of 8 with a sulfonyl chloride compound under similar conditions. Also standard amide coupling techniques can be used to form an amide group at the free amine. Techniques for these procedures are well known to those skilled in the art. Deprotection of the Boc amine of 8 or 9 followed by trapping with the appropriate electrophile gives inhibitors 10 and 11. Again the generation of the sulfonamide is shown for illustrative purposes, but as above for compounds 8 and 9, one skilled in the art will appreciate that similar structures can be prepared in a like manner.

Scheme III shows the preparation of compounds wherein X is —$CH_2$— (compound 14).

Scheme III

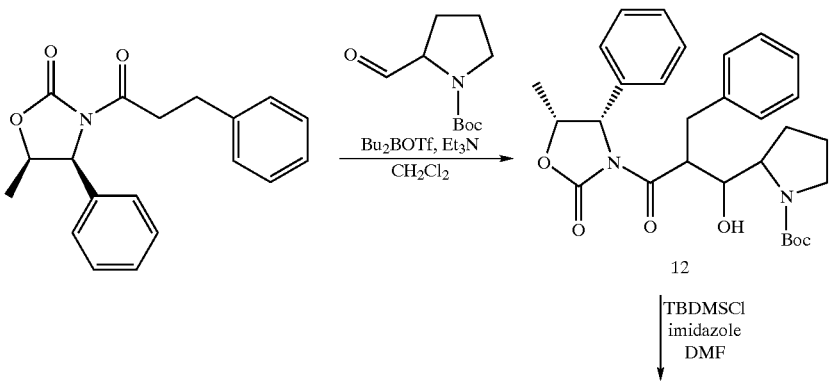

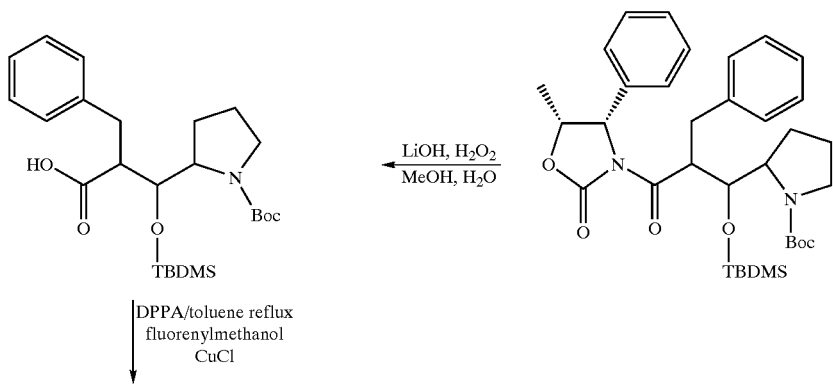

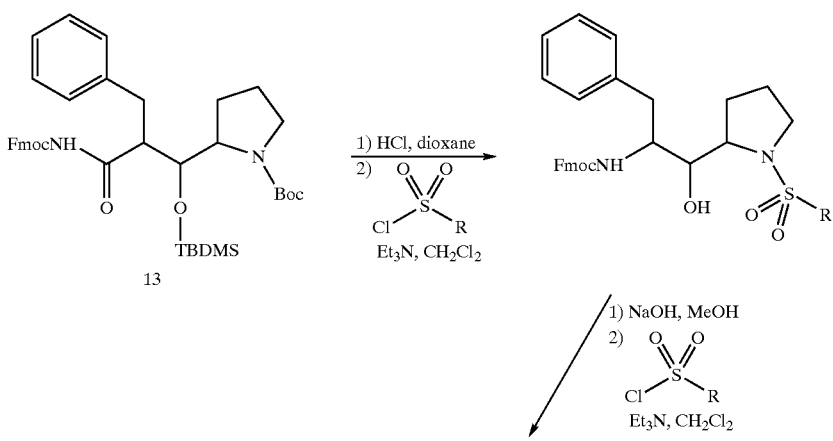

Asymmetric aldol condensation using the known procedure (G. R. Pettit et al., "The Dolastatins; 18: Stereospecific Synthesis of Dolaproine", Synthesis, P 719 (1996)) generates the alcohol 12. Oxidative removal of the chiral auxiliary followed by Curtius rearrangement gives cyclic carbamate 13. Deprotection of the pyrrolidine nitrogen and reaction with the appropriate electrophile, followed by removal of the cyclic carbamate using NaOH in methanol, and reaction of the resulting primary amine with the appropriate electrophile gives inhibitor 14.

In both nitrogen substitutions, as above for compounds 8 and 9, the generation of the sulfonamide is shown for illustrative purposes, but as above one skilled in the art will appreciate that similar structures can be prepared in a like manner. The compounds of this invention are also illustrated by Table I which follows. In this table, activity is characterized as "A" if the $IC_{50}$ is below 5 $\mu$M, "B" if the $IC_{50}$ is between 5 $\mu$M and 20 $\mu$M, and "C" if the $IC_{50}$ is greater than 20 $\mu$M.

TABLE 1

| Compound | R | E | Activity (μM) |
|---|---|---|---|
| EP-001134 | Boc | 4-F-phenyl | A |
| EP-001153 | Boc | quinolin-8-yl | B |
| EP-001155 | Boc | 4-OCF₃-phenyl | B |
| EP-001156 | Boc | phenyl | A |
| EP-001157 | Boc | 4-NO₂-phenyl | A |
| EP-001158 | Boc | 3-bromo-2-chloropyridin-5-yl | B |
| EP-001159 | Boc | 4-isopropylphenyl | B |
| EP-001161 | 1-(3-hydroxy-2-methylphenyl)ethan-1-one-1-yl | 4-F-phenyl | A |
| EP-001162 | 1-(2,6-dimethylphenoxy)propan-2-on-1-yl | 4-F-phenyl | A |

TABLE 1-continued
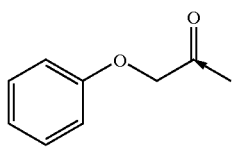
| Compound | R | E | Activity (μM) |
|---|---|---|---|
| EP-001163 | 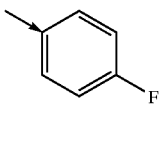 | 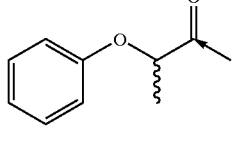 | C |
| EP-001164 | 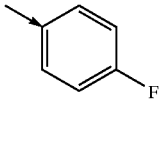 | 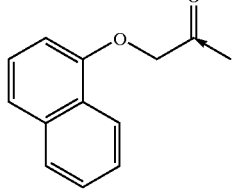 | C |
| EP-001165 | 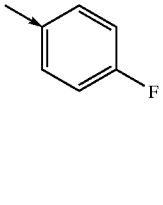 | 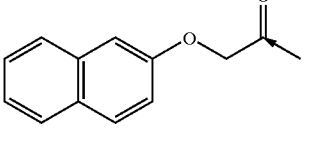 | C |
| EP-001166 | 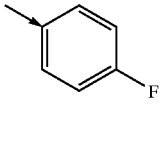 | 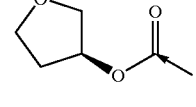 | C |
| EP-001169 | 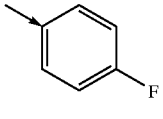 | 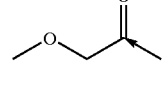 | A |
| EP-001170 | 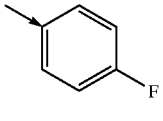 | 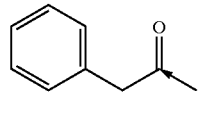 | A |
| EP-001171 | 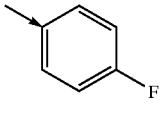 | 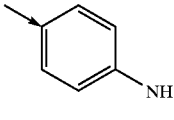 | C |
| EP-001172 | Boc | 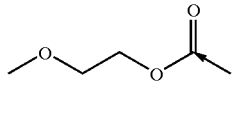 | A |
| EP-001184 | 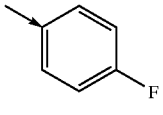 |  | A |

TABLE 1-continued

| Compound | R | E | Activity (μM) |
|----------|---|---|---------------|
| EP-001195 | (2-methyl-3-hydroxybenzoyl) | (4-aminophenyl) | A |

The compounds of this invention may be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

As discussed above, the compounds of the present invention are excellent ligands for aspartyl proteases, particularly HIV-1 and HIV-2 proteases, although renin, endothelin, cathepsin D and plasmepsin may also be inhibited. As protease inhibitors, these compounds are capable of targeting and inhibiting late stage events in HIV replication, i.e., the processing of the viral polyproteins by HIV encoded proteases. Such compounds inhibit the proteolytic processing of viral polyprotein precursors by inhibiting aspartyl protease. Because aspartyl protease is essential for the production of mature virions, inhibition of that processing effectively blocks the spread of virus by inhibiting the production of infectious virions, particularly from chronically infected cells. A further embodiment of the present invention is a method of treating HIV infection, or inhibiting HIV replication, comprising administering to a mammal in need of treatment an HIV inhibiting dose of a compound of the invention or a pharmaceutically acceptable salt or solvate thereof.

The term "pharmaceutically acceptable salt" refers to salts prepared from pharmaceutically acceptable non-toxic acids or bases including inorganic acids and bases and organic acids and bases. When the compounds of the present invention are basic, salts may be prepared from pharmaceutically acceptable non-toxic acids including inorganic and organic acids. Suitable pharmaceutically acceptable acid addition salts for the compounds of the present invention include acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. When the compounds contain an acidic side chain, suitable pharmaceutically acceptable base addition salts for the compounds of the present invention include metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine.

The term "effective amount" as used herein, means an amount of a compound of the present invention which is capable of inhibiting the HIV protease mediated viral component production and assembly. The HIV protease inhibition contemplated by the present method includes both therapeutic and prophylactic treatment, as appropriate. Methods of treatment, their dosage levels and requirements may be selected by those of ordinary skill in the art from available methods and techniques. For example, a compound of this invention may be combined with a pharmaceutically acceptable adjuvant for administration to a virally-infected patient in a pharmaceutically acceptable manner and in an amount effective to lessen the severity of the viral infection. Alternatively, the compounds of this invention may be used in vaccines and methods for protecting individuals against viral infection over an extended period of time. The compounds may be employed in such vaccines either alone or together with other compounds of this invention in a manner consistent with the conventional utilization of protease inhibitors in vaccines. For example, a compound of this invention may be combined with pharmaceutically acceptable adjuvants conventionally employed in vaccines and administered in prophylactically effective amounts to protect individuals over an extended period time against HIV infection. As such, the protease inhibitors of this invention can be administered as agents for treating or preventing HIV infection in a mammal.

The term "pro-drug" as used herein refers to pharmacologically acceptable derivatives, for example, but not limited to, esters and amides, such that the resulting biotransformation product of the derivative is the active drug. Pro-drugs are known in the art and are described generally in, e.g., Goodman and Gilman's "Biotransformation of Drugs," in the Pharmacological Basis of Therapeutics, 8th Ed., McGraw Hill, Int. Ed. 1992, page 13–15, which is hereby incorporated by reference in its entirety.

The compounds of this invention may be administered to a healthy or HIV-infected patient either as a single agent or in combination with other anti-viral agents which interfere with the replication cycle of HIV. By administering the compounds of this invention with other anti-viral agents which target different events in the viral life cycle, the therapeutic effect of these compounds is potentiated. For instance, the co-administered anti-viral agent can be one which targets early events in the life cycle of the virus, such as cell entry, reverse transcription and viral DNA integration into cellular DNA. AntiHIV agents targeting such early life cycle events include, didanosine (ddI), alcitabine (ddC), d4T, zidovudine (AZT), polysulfated polysaccharides, sT4 (soluble CD4), ganiclovir, dideoxycytidine, trisodium phosphonoformate, eflornithine, ribavirin, acyclovir, alpha interferon and trimenotrexate. Additionally, non-nucleoside inhibitors of reverse transcriptase, such as TIBO or nevirapine, may be used to potentiate the effect of the compounds of this invention, as may viral uncoating inhibitors, inhibitors of trans-activating proteins such as tat or rev, or inhibitors of the viral integrase. Combination therapies according to this invention exert a synergistic effect in inhibiting HIV replication because each component agent of the combination acts on a different site of HIV replication. The use of such combinations also advantageously reduces the dosage of a given conventional anti-retroviral agent which would be required for a desired therapeutic or prophylactic effect as compared to when that agent is administered as a monotherapy. Combinations may reduce side effects while maintaining anti-retroviral activity, or they may increase efficacy without increasing toxicity. Combinations also reduce potential of resistance to single agent therapies, while minimizing any associated toxicity.

In particular, we have discovered that these compounds act synergistically in preventing the replication of HIV in human T cells. Preferred combination therapies include the administration of a compound of this invention with AZT, ddI, ddC or d4T. Alternatively, the compounds of this invention may also be co-administered with other HIV protease inhibitors such as Ro 31-8959 (Roche), L-735,524 (Merck), XM 323 (Du-Pont Merck) and A-80,987 (Abbott) to increase the effect of therapy or prophylaxis against various viral mutants or members of other HIV quasi species.

Particularly preferred classes of agents for use in combination with the inventive compounds include other antiviral agents such as other protease inhibitors and reverse transcriptase inhibitors of the nucleoside, non-nucleoside, or nucleotide analog variety. Other preferred classes of antiviral agents include fusion inhibitors, zinc finger inhibitors, integrase inhibitors, cellular inhibitors, and molecules that block HIV receptors such as the CD4, CCR5, CXCR4 receptors, etc. Many of the preferred combinations include at least three agents. For example, certain preferred combinations will include one or more compounds of the present invention together with one or more other protease inhibitors together with one or more reverse transcriptase inhibitors.

Particularly preferred retroviral protease inhibitors include those currently approved by the FDA such as saquinavir, ritonavir, indinavir, nelfinavir, and amprenavir and investigational agents such as tipranivir (PNU-140690), lopinavir (ABT-378), BMS-234475, DMP-450, L-756,423, AG1776, and PD-178390. Preferred reverse transcriptase inhibitors include the FDA-approved NRTIs zidovudine (ZDV,AZT), didanosine (dideoxyinosine, ddI), zalcitabine (dideoxycytidine; ddC), stavudine (d4T), lamivudine (3TC), and abacarir (ABC), the investigational NRTIs emtricitabine (FTC), dOTC, and dAPD, the FDA-approved NNRTIs nevirapine (NVP), delavirdine (DLV), and efavirenz (EFZ), the investigational NNRTIs emivirine, (MKC442), capravirine (AG 1549), DMP/DPC 961, DMP/DPC 963), calanolide A, GW420967X, and PNU142721, and the nucleotide analogs adefovir (ADV) and tenofovir. Other preferred agents include fusion inhibitors such as T-20, peptide 2, T-1249, AMD-3100, PRO542, FP-21399, rCD4/CD4-OgG, and CD4-PE40, zinc finger inhibitors such as ADA, cellular inhibitors such as hydroxyurea (HU), peldesine (Bcx-34), and topotecan.

Additional agents of potential utility in combination with the inventive compounds include the protease inhibitor Ro 31-8959, SC-52151, KNI-227, KNI-272 and the like, reverse transcriptase inhibitors such as R82193, L-697,661, HEPT compounds, L,697,639, R-82150, U-87201E and the like, Bch-189, AzdU, carbovir, DDA, D4C, DP-AZT,FLT (fluorothymidine), BCG-189, 5-halo-3'-thiadideoxycytidine, PMEA, TAT inhibitors (for example, RO-24-7429 and the like). AL-721, polymannoacetate, trisodium phosphonoformate, HPA-23, eflonithine, Peptide T, Reticulose (nucleophosphoprotein), ansamycin LM 427, trimetrexate, UA001, ribavirin, oxetanocin, oxetanocin-G, cylobut-G, cyclobut-A, ara-M, BW882C87, oscarnet, BW256U87, BW348U87, L-69,989, BV ara-U, CMV triclonal antibodies, FIAC, HOE-602, HPMPC, MSL-109, TI-23, trifluridine, vidarabine, famciclovir, penciclovir, acyclovir, ganciclovir, castanospernine, butyl-DNJ, hypericin, oxamyristic acid, dextran sulfate and pentosan polysulfate.

Immunomodulators that can be administered in combination with a compound of the present invention include bropirimine, Ampligen, anti-human alpha interferon antibody, CL246,738, Imreg-1, Imreg-2, diethydithiocarbamate, interleukin-2, interleukin-3, interleukin-4, alpha interferon, beta interferon, gamma interferon, inosine pranobex, methionine enkephalin, muramyl-tripeptide, TP-5, erythropoietin, naltrexone, tumor necrosis factor, FK-565, FK-506, GM-CSF, alpha interferon immunoglobulin, IGF-1, anti-Leu-3A, isopinosine, IVIG, and HIVIG. Certain techniques for immunomodulation, such as autologous CD8+infusion, autovaccination, biostimulation, extracorporeal photophoresis, hyperthermia, passive immunotherapy and polio vaccine hyperimmunization may also be used with the compounds of the invention.

Any of a variety of HIV or AIDS vaccines, for example gp120 (recombinant), Env2-3 (gp120), HGP-30, HIV-Immunogen, p24 (recombinant) and VaxSyn HIV-1 (p24), can be used in combination with a compound of the present invention. We prefer administering the compounds of this invention as single agents or in combination with retroviral reverse transcriptase inhibitors, such as derivatives of AZT, or other HIV aspartyl protease inhibitors. The compounds of this invention can also be administered in combination with antibiotics (e.g., pentamidine isethiorate) to prevent or combat infection and disease associated with HIV infections, such as AIDS and ARC.

When the compounds of this invention are administered in combination therapies with other agents, they may be administered sequentially or concurrently to the patient. Alternatively, pharmaceutical or prophylactic compositions according to this invention may be comprised of a combination of an aspartyl protease inhibitor of this invention and another therapeutic or prophylactic agent.

Although this invention focuses on the use of the compounds disclosed herein for preventing and treating HIV infection, the compounds can also be used as inhibitory agents for other viruses which depend on similar aspartyl proteases for obligatory events in their life cycle. These viruses include, as well as other AIDS-like diseases caused by retroviruses, such as simian immunodeficiency viruses, but are not limited to, HTLV-I and HTLV-II.

Pharmaceutical compositions of this invention comprise any of the compounds of the present invention, and pharmaceutically acceptable salts thereof, with any pharmaceutically acceptable carrier, adjuvant or vehicle. Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of this invention may be administered orally, parenterally, by inhalation, topically, rectally, nasally, buccally, vaginally or via an implanted reservoir. We prefer oral administration or administration by injection. The pharmaceutical compositions of this invention may contain any conventional non-toxic pharmaceutically-acceptable carriers, adjuvants or vehicles. The term parenteral as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as Ph. Helv or a similar alcohol.

The pharmaceutical compositions of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The specific dose of compound administered according to this invention to obtain therapeutic and/or prophylactic effects will, of course, be determined by the particular circumstances surrounding the case, including, for example, the compound administered, the route of administration, and the condition being treated. Dosage levels of between about 0.01 and about 100 mg/kg body weight per day, preferably between about 0.5 and about 50 mg/kg body weight per day and ideally from about 0.1 to about 10 mg/kg body weight per day of the active ingredient compound are useful in the prevention and treatment of viral infection, including HIV infection. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms. As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the infection, the patient's disposition to the infection and the judgment of the treating physician.

The compounds of this invention are also useful as commercial reagents which effectively bind to aspartyl proteases, particularly HIV aspartyl protease. As commercial reagents, the compounds of this invention, and their derivatives, may be used to block proteolysis of a target peptide or may be derivatized to bind to a stable resin as a tethered substrate for affinity chromatography applications. These and other uses which characterize commercial aspartyl protease inhibitors will be evident to those of ordinary skill in the art.

The following Preparations and Examples further illustrate the compounds of the present invention and methods for the synthesis. The examples are not intended to be limiting to the scope of the invention in any respect and should not be so construed.

Abbreviations and Definitions

The following abbreviations and terms have the indicated meanings throughout:

| | |
|---|---|
| Ac = | acetyl |
| BNB = | 4-bromomethyl-3-nitrobenzoic acid |
| Boc = | t-butyloxy carbonyl |
| Bu = | butyl |
| c- = | cyclo |
| DBU = | diazabicyclo[5.4.0]undec-7-ene |
| DCM = | dichloromethane = methylene chloride = $CH_2Cl_2$ |
| DEAD = | diethyl azodicarboxylate |
| DIBAL = | diisobutyl aluminum hydride |
| DIC = | diisopropylcarbodiimide |
| DIEA = | N,N-diisopropylethyl amine |
| DMAP = | 4-N,N-dimethylaminopyridine |
| DMF = | N,N-dimethylformamide |
| DMSO = | dimethyl sulfoxide |
| DPPA = | diphenylphosphoryl azide |
| DVB = | 1,4-divinylbenzene |
| EDCI = | 1-(3-dimethylaminopropyl)-3-ethylcarbodiimide |
| EEDQ = | 2-ethoxy-1-ethoxycarbonyl-1,2-dihydroquinoline |
| Fmoc = | 9-fluorenylmethoxycarbonyl |
| GC = | gas chromatography |
| HATU = | O-(7-Azabenzotriazol-1-yl)-1,1,3,3,-tetramethyluronium hexafluorophosphate |
| HOAc = | acetic acid |
| HOBt = | hydroxybenzotriazole |
| Me = | methyl |
| mesyl = | methanesulfonyl |
| MTBE = | methyl t-butyl ether |
| NMO = | N-methylmorpholine oxide |
| PEG = | polyethylene glycol |
| Ph = | phenyl |
| PhOH = | phenol |
| PfP = | pentafluorphenol |
| PPTS = | pyridium p-toluenesulfonate |
| PyBroP = | bromo-tris-pyrrolidino-phosphonium hexafluorophosphate |
| rt = | room temperature |
| sat'd = | saturated |
| TBDMS = | t-butyldimethylsilyl |
| TFA = | trifluoroacetic acid |
| THF = | tetrahydrofuran |
| TMOF = | trimethyl orthoformate |
| TMS = | trimethylsilyl |
| tosyl = | p-toluenesulfonyl |
| Trt = | triphenylmethyl |

General Materials and Methods

Unless otherwise noted, NMR data appearing in the examples refers to the free base or free acid of the subject compound. In the following Preparations and Examples, the terms melting point, nuclear magnetic resonance spectra, electrospray mass spectra, infrared spectra, ultraviolet spectra, elemental analysis, specific rotation, high performance liquid chromatography, and thin layer chromatography are abbreviated m.p., n.m.r, m.s., i.r., u.v., anal., o.r., HPLC, and TLC, respectively. In addition, the absorption maxima listed for the i.r. spectra are only those of interest and not all of the maxima observed. In conjunction with n.m.r. spectra, the following abbreviations are used: "s" is singlet, "d" is doublet, "dd" is doublet of doublets, "t" is triplet, "q" is quartet, "m" is multiplet, "dm" is a doublet of multiplets and "br.s", "br.d", "br.t", and "br.m" are broad singlet, doublet, triplet, and multiplet respectively.

Thin layer chromatography (TLC) was carried out using 0.25 mm thick E. Merck silica gel 60 F254 plates and elution with the indicated solvent system. Detection of the compounds was carried out by treating the plate with an appropriate visualizing agent, such as 10% solution of phosphomolybdic acid in ethanol or a 0.1% solution of ninhydrin in ethanol, followed by heating, and/or by exposure to UV light or iodine vapors when appropriate. Thick layer silica gel chromatography was also carried out using E. Merck 60 F254 plates ("prep plates") of 0.5, 1.0, or 2.0 mm thickness. Following development of the plate, the band of silica containing the desired compound was isolated and eluted with an appropriate solvent. Melting points are uncorrected.

Insofar as compounds of the invention are able to inhibit the replication of the HIV virus in human T-cells and furthermore, may be delivered orally to mammals, they are of evident clinical utility for the treatment of HIV infection. These tests are predictive of the compounds ability to inhibit HIV protease in vivo. We have measured the inhibition constants of each compound against HIV-1 protease using essentially the method described by M. W. Pennington et al., *Peptides* 1990, Gimet, E. and D. Andrew, Eds., Escom; Leiden, Netherlands (1990).

EXAMPLES

Compound 2:

In a dry round bottom flask under nitrogen 50 g (0.188 mol) of Boc phenylalanine was dissolved in 500 mL of methylene chloride and 25 mL (0.228 mol) of N-methyl-morpholine was added. The reaction was cooled to −20° C. and isobutylchloroformate (23.3 mL, 0.180 mol) was added drop wise. The reaction was warmed to 0° C. and allowed to stir for 30 min. In a separate flask 15.8 g (0.189 mol) of Dimethylhydroxylamine HCL was dissolved in 100 mL of DMF and 300 mL of methylene chloride was added followed by 25 mL (0.228 mol) of N-methyl-morpholine. The mixture was allowed to stir for 30 min. and the white HCl salt of N-methyl morpholine precipitates after~30 sec. After the appropriate time, the amine was added via cannula to the Boc phenylalanine mixed anhydride at 0° C. After all the liquid has been transferred, the solids were poured into the reaction vessel with the aid of 50 ml of dry methylene chloride. The reaction was allowed to warm to room temperature over 3 h. and then poured into 200 mL of 1 N HCl. The layers were separated and the aqueous layer was washed with three 200 mL portions of methylene chloride. The combined organics were dried over $Na_2CO_3$ and then condensed in vacuo. The resulting residue containing DMF was re dissolved in Ethyl acetate 800 mL and washed with two 200 mL portions of 1 N HCl, two 200 mL portions of saturated $NaHCO_3$, 200 mL of water and 200 mL of brine. The organic layer was then dried over $Na_2CO_3$ and condensed in vacuo. The resulting yellowish viscous oil was used without further purification.

Yield=56.3 g (97%)

Compound 3:

In a dry round bottom flask under nitrogen 12 g (0.50 mol) of magnesium powder was slurried in 10 mL of dry THF then 418 mL (0.418 mol) of vinyl bromide (1M in THF) was added at such a rate as to maintain a gentle boil. After the bromide has been added (~1 h) the reaction was stirred a further 30 min. Meanwhile in a separate flask 51.5 g (0.167 mol) of the Weinreb amide was dissolved in 500 mL of THF in a second dry round bottom flask and cooled to 0° C. in an ice bath. The vinyl Grignard was added via cannula and the reaction was allowed to stir at 0° C. for 3 hours and at room temperature for 20 hours. After the reaction was complete it was poured slowly into a mixture of 2 N HCl (500 mL) and ice 200 g (gas evolution!). The quench was maintained strongly acidic through out and excess HCl was added if needed. The mixture was transferred to a seperatory funnel and the layers were separated. The aqueous layer was washed with three 200 mL portions of ethyl acetate and the combined organics were dried over $Na_2SO_4$. The solvent was removed to a volume of 100 mL and 500 mL of hexane was added. The solution was treated with 5 g of charcoal and passed through a 100×70 cm plug of silica using 10% ethyl acetate in hexanes (300 mL) as an eluant. The resulting light yellow material was cooled overnight and the white crystals which form were collected by vacuum filtration and washed with cold (−20° C.) hexanes to give 21.6 g of product. A further 14.6 g of product can be obtained by concentrating the mother liquor dissolving the resulting yellow oil in 10% ethyl acetate in hexanes (100 mL) and passing through a second silica gel plug using 10% ethyl acetate in hexanes (300 mL) as an eluant.

Yield=36.2 g (78%)

Compound 4:

In a dry round bottom flask under nitrogen 39 g (0.141 mol) of the enone was dissolved in 700 mL of dry methylene chloride and cooled to −78° C. DIBAL (212 mL, 0.212 mol) was added at a rate of 20 mL/h. Care was taken not to allow the internal temperature to rise above −60° C. After addition was complete the reaction was followed by TLC ($SIO_2$, 30% ethyl acetate in hexanes) and was complete in 2 h at −78° C. The excess DIBAL was quenched by addition of isopropanol (5 mL) at −78° C. and the reaction was allowed to warm to 0° C. at which point it was poured into 1L of 1 N Rochelle's salt and allowed to stir overnight. The layers were separated and the aqueous phase was extracted with two 200 mL portions of methylene chloride. The combined organics were washed with 300 ML of brine and dried over $Na_2SO_4$. The solvent was removed in vacuo and the resulting sticky white solid was recrystallized from $Et_2O$ and hexanes.

Yield=26.2 g (67%)

Compound 5:

To a solution of compound 4 (5.54 g, 20 mmol) in 50 mL pyridine was added acetic anhydride (20 mL, ~0.2 mol) at room temperature. The reaction mixture was stirred at room temperature for 16 hours. Ethyl acetate (300 mL) was added and the mixture was washed with 2N HCl (200 mLX3), brine (200 mL) and $NaHCO_3$ (200 mL). Dried over $Na_2SO_4$ and concentrated. The residue was recrystallized from EtOAc and Hexane to give product 6.2 g (98%). H NMR (CDCl3): 7.23 (m, 5H), 5.81 (ddd, 1H), 5.30 (m, 3H), 4.42 (d, 1H), 4.18 (bs, 1H), 2.86 (dd, 1H), 2.63 (m, 1H), 2.06 (s, 3H), 1.32 (s, 9H).

Compound 15:

To a solution of compound 5 (3.19 g, 10 mmol) in 50 mL $CH_2Cl_2$ and 15 mL methanol was bubbled in ozone at −78° C. until the solution became light blue. Then the nitrogen was bubbled in to remove excess ozone. $PPh_3$ (1.3 equiv.) was added and the mixture was warmed to room temperature and stirred for 3 hrs. Concentration and chromotographed on silica gel (EtOAc: Hexane=1:4) to give product 3.2 g (99%).

H NMR (CDCl3): 9.35 (s, 1H), 7.24 (m, 5H), 5.08 (d, 1H), 4.63 (bs, 1H), 4.42 (bs, 1H). 2.84 (d, 2H), 2.20 (s, 1H), 1.34 (s, 9H).

Compound 6:

2-Aminoethanethiol hydrochloride (171 mg, 1.5 mmol) was dissolved in 3 mL 0.5N NaOH. To this solution was added a solution of compound 6 (321 mg, 1 mol) in 6 mL of ethanol. The mixture was stirred at room temperature for 2 hrs. Extraction with ethyl acetate (20 mL) and washed with brine (30 mLX2). Dried over $Na_2SO_4$ and concentrated. The residue was chromatographed on silica gel to give product (350 mg). ESMS: 339.13 (M+1).

EP-001134:

To a solution of compound 6 (135.2 mg, 0.4 mmol) in 7 mL of dichloromethane was added 4-flurobenzenesulfonyl chloride (93.7 mg, 0.5 mmol) and triethyl amine (85 μL, 0.6 mmol) at room temperature. The mixture was stirred at room temperature for 14 hrs. Washed with 1N HCl (10 mL), brine (10 mL) and NaHCO3 (10 mL) and dried over $Na_2SO_4$. Concentrated and the residue was chromatographed on silica gel to give product (120 mg). ESMS: 496.54 (M+1); 518.51 (M+23)

EP-001153:

Using substantially the same procedure as for EP-001134 compound 6 (135.2 mg, 0.4 mmol), 8-quinolinesulfonyl chloride (114 mg, 0.5 mmol) and triethyl amine (85 μL, 0.6 mmol) were combined. The resulting material was chromatographed on silica gel to give product (130 mg)

EP-001155:

Using substantially the same procedure as for EP-001134 compound 6 (135.2 mg, 0.4 mmol, 4-trifluoromethoxybenzenesulfonyl chloride (131 mg, 0.5 mmol) and triethyl amine (85 μL, 0.6 mmol) were combined. The resulting material was chromatographed on silica gel to give product (125 mg). ESMS: 563.21 (M+1).

EP-001156:

Using substantially the same procedure as for EP-001134 compound 6 (135.2 mg, 0.4 mmol), benzenesulfonyl chloride (89 mg, 0.5 mmol) and triethyl amine (85 μL, 0.6 mmol) were combined. The resulting material was chromatographed on silica gel to give product (115 mg). ESMS: 501.39 (M+23).

EP-001157:

Using substantially the same procedure as for EP-001134 compound 6 (135.2 mg, 0.4 mmol), 4-nitrobenzenesulfonyl chloride (111 mg, 0.5 mmol) and triethyl amine (85 μL, 0.6 mmol) were combined. The resulting material was chromatographed on silica gel to give product (110 mg)

EP-001172:

To a solution of compound EP-001157 (50 mg) in 5 mL ethanol was added $PtO_2$ (5 mg). The mixture was stirred at room temperature under $H_2$ atmosphere for 16 hrs. Filtration and the filtrate was condensed and chromotographyed on silica gel to give product (43 mg). ESMS: 516.60 (M+Na); 530.60 (M+39)

EP-001158:

Using substantially the same procedure as for EP-001134 compound 6 (135.2 mg, 0.4 mmol), 3-bromo-2-chloropyridine-5-sulfonyl chloride (146 mg, 0.5 mmol) and triethyl amine (85 μL, 0.6 mmol) were combined. The resulting material was chromatographed on silica gel to give product (100 mg). ESMS: 492.03 (M+1).

EP-001159:

Using substantially the same procedure as for EP-001134 compound 6 (135.2 mg, 0.4 mmol), 4-isopropylbenzenesulfonyl chloride (110 mg, 0.5 mmol) and triethyl amine (85 μL, 0.6 mmol) were combined. The resulting material was chromatographed on silica gel to give product (115 mg). ESMS: 543.45 (M+23)

EP-001161:

To compound EP-001134 (124 mg, 0.25 mmol) was added 3 mL of 6N HCl in dioxane. The mixture was stirred at room temperature for 30 min. Concentrated and the residue was added 4 mL of dichloromethane and NMM (280 μL, 1 mmol). Then 2-methyl3-hydroxylbenzoic acid (46 mg, 0.3 mmol) was added followed by HOBT (106 mg, 0.7 mmol) and EDCI (133 mg, 0.7 mmol). The solution was stirred at room temperature for 16 hrs. Diluted with ethyl acetate and then washed with 1N HCl (30 mL), brine (30 mL) and NaHCO$_3$ (30 μL). Dried over Na$_2$SO$_4$. Concentrated and the residue was chromatographed on silica gel to give product (110 mg).

EP-001163:

Using substantially the same procedure as for EP-001161 compound EP-001134 (124 mg, 0.25 mmol), NMM (280 μL, 1 mmol), phenoxy acetic acid (44 mg, 0.3 mmol), HOBT (106 mg, 0.7 mmol) and EDCI (133 mg, 0.7 mmol were combined The resulting material was chromatographed on silica gel to give product (115 mg). ESMS: 531.11 (M+1).

EP-001164:

Using substantially the same procedure as for EP-001161 compound EP-001134 (124 mg, 0.25 mmol), NMM (280 μL, 1 mmol), 2-phenoxypropionic acid (46 mg, 0.3 mmol), HOBT (106 mg, 0.7 mmol) and EDCI (133 mg, 0.7 mmol were combined. The resulting material was chromatographed on silica gel to give product (100 mg). ESMS: 545.12 (M+1).

EP-001165:

Using substantially the same procedure as for EP-001161 compound EP-001134 (124 mg, 0.25 mmol), NMM (280 μL, 1 mmol), 1-naphthoxy acetic acid (52 mg, 0.3 mmol), HOBT (106 mg, 0.7 mmol) and EDCI (133 mg, 0.7 mmol were combined. The resulting material was chromatographed on silica gel to give product (120 mg). ESMS: 581.24 (M+1).

EP-001166:

Using substantially the same procedure as for EP-001161 compound EP-001134 (124 mg, 0.25 mmol), NMM (280 μL, 1 mmol), 2-naphthoxy acetic acid (52 mg, 0.3 mmol), HOBT (106 mg, 0.7 mmol) and EDCI (133 mg, 0.7 mmol were combined. The resulting material was chromatographed on silica gel to give product (120 mg). ESMS: 581.19 (M+1).

EP-001169:

To compound EP-001134 (124 mg, 0.25 mmol) was added 3 mL of 6N HCl in dioxane. The mixture was stirred at room temperature for 30 min. Concentrated and the residue was added 4 mL of dichloromethane and NMM (280 μL, 1 mmol). Then THF chloroformate (0.25 mmol) was added and the mixture was stirred at room temperature for 3 hrs. Diluted with ethyl acetate and then washed with 1N HCl (30 mL), brine (30 mL) and NaHCO$_3$ (30 mL). Dried over Na$_2$SO$_4$. Concentrated and the residue was chromatographed on silica gel to give product (100 mg). ESMS: 511.54 (M+1); 533.54 (M+Na).

EP-001170:

To compound EP-001134 (124 mg, 0.25 mmol) was added 3 mL of 6N HCl in dioxane. The mixture was stirred at room temperature for 30 min. Concentrated and the residue was added 4 mL of dichloromethane and NMM (280 μL, 1 mmol). Then ethyl chloroformate (0.25 mmol) was added and the mixture was stirred at room temperature for 3 hrs. Diluted with ethyl acetate and then washed with 1N HCl (30 mL), brine (30 mL) and NaHCO$_3$ (30 mL). Dried over Na$_2$SO$_4$. Concentrated and the residue was chromatographed on silica gel to give product (95 mg). ESMS: 469.47 (M+1); 491.47 (M+Na).

EP-001171:

Using substantially the same procedure as for EP-001161 compound EP-001134 (124 mg, 0.25 mmol), NMM (280 μL, 1 mmol), phenyl acetic acid (42 mg, 0.3 mmol), HOBT (106 mg, 0.7 mmol) and EDCI (133 mg, 0.7 mmol were combined. The resulting material was chromatographed on silica gel to give product (110 mg). ESMS: 515.51 (M+1); 537.52 (M+Na).

EP-001184:

To compound EP-001134 (124 mg, 0.25 mmol) was added 3 mL of 6N HCl in dioxane. The mixture was stirred at room temperature for 30 min. Concentrated and the residue was added 4 mL of dichloromethane and NMM (280 μL, 1 mmol). Then (2-methoxy)ethyl chloroformate (0.25 mmol) was added and the mixture was stirred at room temperature for 3 hrs. Diluted with ethyl acetate and then washed with 1N HCl (30 mL), brine (30 mL) and NaHCO$_3$ (30 μL). Dried over Na$_2$SO$_4$. Concentrated and the residue was chromatographed on silica gel to give product (100 mg). ESMS: 499.57 (M+1); 521.51 (M+Na).

EP-001195:

To compound EP-001157 (131 mg, 0.25 mmol) was added 3 mL of 6N HCl in dioxane. The mixture was stirred at room temperature for 30 min. Concentrated and the residue was added 4 mL of dichloromethane and NMM (280%L, 1 mmol). Then 2-methyl3-hydroxylbezoic acid (46 mg, 0.3 mmol) was added followed by HOBT (106 mg, 0.7 mmol) and EDCI (133 mg, 0.7 mmol). The solution was stirred at room temperature for 16 hrs. Diluted with ethyl acetate and then washed with 1N HCl (30 mL), brine (30 mL) and NaHCO$_3$ (30 mL). Dried over Na$_2$SO$_4$. Concentrated and the residue was dissolved in 6 mL of methanol. To the solution was added PtO$_2$ (15 mg) and the suspension was stirred at room temperature under H$_2$ atmosphere for 16 hrs. Filtration and the filtrate was condensed and chromatographed on silica gel to give product (90 mg). ESMS: 528.60 (M+1); 550.65 (M+Na).

Biological Assay for Inhibition of Microbial Expressed Viral Protease

The inhibition constants against HIV-1 protease were measured using the method described by M. V. Toth and G. R. Marshall, *Int. J. Peptide protein Res.*, 1990, 544. The method described M. W. Pennington et al., Peptides 1990, Gimet, E. and D. Andrew, Eds., Escom; Leiden, Netherlands (1990) may also be used. Inhibition is measured as IC$_{50}$ in μM. The person of skill would accept these tests as predictive of the compounds' utility in vivo to treat HIV infected patients.

While a number of embodiments of this invention are described, it is apparent that individual structures may be altered to provide other embodiments which still fall within the inventive concept. Therefore, it will be appreciated that the scope of this invention is to be defined by the appended claims, rather than by the specific embodiments which have been presented by way of example.

What is claimed is:

1. A compound of the formula:

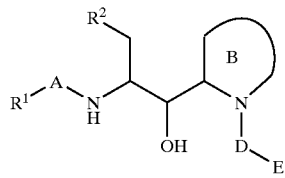

wherein:
R$^1$ is chosen from the group consisting of C$_1$–C$_{20}$ alkyl, aryl, alkylaryl, substituted alkylaryl, C$_1$–C$_{10}$ alkoxy, C$_1$–C$_{10}$ oxaalkyl, aryloxy, substituted aryl, substituted aryloxy, heterocyclyl and heterocyclyloxy;

R$^2$ is chosen from the group consisting of C$_1$–C$_{10}$ hydrocarbon, substituted aryl and heterocyclyl;

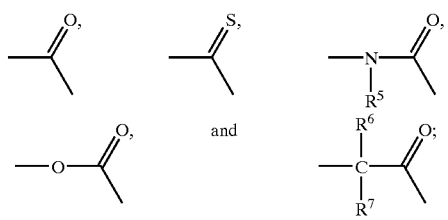

A is chosen from the group consisting of a direct bond, —SO$_2$—, NHSO$_2$—,

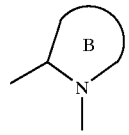

is thiazolidine;

R$^5$, R$^6$ and R$^7$ are chosen from the group consisting of hydrogen and lower alkyl;

D is —SO$_2$—; and

E is chosen from the group consisting of C$_1$–C$^{10}$ hydrocarbon, substituted aryl, heterocyclyl and substituted heterocyclyl.

2. A compound according to claim 1 wherein E is chosen from aryl, heteroaryl, substituted aryl and substituted heteroaryl.

3. A pharmaceutical composition comprising a pharmaceutically acceptable carrier and a compound according to claim 1, or a pharmaceutically acceptable salt or solvate thereof.

4. A pharmaceutical composition according to claim 3 comprising at least one additional antiviral agent.

* * * * *